United States Patent [19]

Dominey

[11] Patent Number: 5,273,840

[45] Date of Patent: Dec. 28, 1993

[54] METHIDE SALTS, FORMULATIONS, ELECTROLYTES AND BATTERIES FORMED THEREFROM

[75] Inventor: Lawrence A. Dominey, Lexington, Mass.

[73] Assignee: Covalent Associates Incorporated, Woburn, Mass.

[21] Appl. No.: 726,642

[22] Filed: Jul. 12, 1991

Related U.S. Application Data

[63] Continuation-in-part of Ser. No. 561,062, Aug. 1, 1990, abandoned.

[51] Int. Cl.$^5$ .......................... H01M 6/16; H01M 6/18
[52] U.S. Cl. .................................. 429/192; 252/62.2
[58] Field of Search ........................ 429/192; 252/62.2

[56] References Cited

U.S. PATENT DOCUMENTS

| | | | |
|---|---|---|---|
| 4,049,861 | 9/1977 | Nozari | 428/220 |
| 4,505,997 | 3/1985 | Armand et al. | 429/192 |
| 4,517,265 | 5/1985 | Belanger et al. | 429/217 |
| 4,739,018 | 4/1988 | Armand et al. | 525/326.2 |
| 4,742,127 | 5/1988 | Armand et al. | 525/354 |
| 4,758,483 | 7/1988 | Armand et al. | 429/192 |
| 4,818,644 | 4/1989 | Armand | 429/192 |
| 4,833,048 | 5/1989 | Dejonghe et al. | 429/104 |
| 4,851,307 | 7/1989 | Armand et al. | 429/192 |
| 4,923,950 | 5/1990 | Ravaine et al. | 528/38 |

FOREIGN PATENT DOCUMENTS 2606217 10/1986 France .

OTHER PUBLICATIONS

Lutz Turowsky and Seppelt, Konrad, "Tris(trifluoromethyl)sulfonyl)-methane, HC(SO$_2$CF$_3$)$_3$", Inorg. Chem. 27, 2135–2137, 1988.

Primary Examiner—Asok Pal
Attorney, Agent, or Firm—Weingarten, Schurgin, Gagnebin & Hayes

[57] ABSTRACT

Salts for use in nonaqueous electrolytes, and electrolytes and electromical generators including such materials. An exemplary compound for use as an electrolyte in an electrochemical cell has the formula

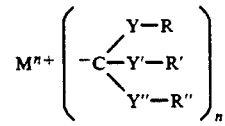

wherein M$^{n+}$ is an ion of Li, Na, K, Ca, Mg, Zn, or Al; each of the moieties Y, Y', and Y'', are >SO$_2$ or >CO; the groups R and R' are separate halogenated alkyl groups of 1–4 carbon atoms, respectively or are joined together to constitute a unitary halogenated alkylene radical of from 2–4 carbon atoms linking Y and Y' and forming a ring structure which includes R, R', Y, Y', and the carbon atom to which Y and Y' are attached; the group R'' is an alkyl or haloalkyl radical of 1–4 carbon atoms or a halogenated phenyl group; n is an integer of 1–3 depending on the identity of the metal M; and metal ion M$^{n+}$ is an ion of Li, Na, Ca, Mg, Zn or Al when each of the Y—R, Y'—R', and Y''—R'' groups is SO$_2$CF$_3$. In another exemplary compound, the —Y''—R'' group is replaced by Z, which is an electron-withdrawing substituent selected from the group consisting of —C(O)H, —NO$_2$, —CN, —F, and perfluorinated alkyls and aryls containing no more than 8 carbons.

28 Claims, 1 Drawing Sheet

FIG. 1

METHIDE SALTS, FORMULATIONS, ELECTROLYTES AND BATTERIES FORMED THEREFROM

STATEMENT OF GOVERNMENT SUPPORT

This invention was made with government support under Grant No. ISI-8660048 awarded by the National Science Foundation. The government has certain rights in this invention.

This application is a continuation-in-part of Dominey, U.S. patent application Ser. No. 07/561,062, filed Aug. 1, 1990, now abandoned, the whole of which is hereby incorporated by reference herein.

FIELD OF THE INVENTION

This invention pertains to electrochemical generators employing typically light metal anodes, and more particularly, to electrolyte salts for use in non-aqueous electrolytes employed therein, and to electrochemical cells or batteries employing such electrolytes.

BACKGROUND OF THE INVENTION

A battery is an electrochemical generator containing one or more galvanic cells in a finished package. Each individual cell is made up of an anode and a cathode made of dissimilar materials and separated by an electrolyte. In operation, the respective electrodes are connected via an external circuit which includes a device in which useful work is to be done, in the case of a discharging cell, or which is capable of doing work on the cell, for the case of a cell which is being recharged. The electrical circuit is completed by the electrolyte, which contains ionic species which transfer charge between the electrodes when the cell is discharging or charging.

Primary batteries are devices initially assembled with high energy chemical compounds, sold in their charged state, and discarded without being recharged after the stored chemical energy has been withdrawn as electrical energy. Secondary batteries are rechargeable devices in which the chemical conditions of the undischarged battery can be restored by applying a current through the cells in the opposite direction from the current flow of the battery in its discharging mode.

The light atomic weight metals employed in light metal anode electrochemical cells are highly electrochemically reducing materials. Their use precludes the use of water or other weakly proton-donating solvents as well as numerous solvents which decompose or fail to form passivating films upon exposure to the anode. Nonaqueous matrices are therefore required in cells employing such light metal anodes. Such nonaqueous matrices may be either nonaqueous liquids or certain polymeric materials in which the conductive salts may be included. Typical solvents include tetrahydrofuran, 2-methyltetrahydrofuran, ethylene carbonate, propylene carbonate, dioxolane, 4-methyldioxolane, 1,2-dimethoxyethane, sulfolane, $\gamma$-butyrolactone, methylformate, methyl acetate, diethylcarbonate, acetonitrile and sulfur dioxide. Commonly used polymeric solvents include numerous polyethers and ether-containing polymers.

The ionizable salts employed in nonaqueous electrolytes have generally utilized anions such as $BF_4^-$, $PF_6^-$, $AsF_6^-$, $ClO_4^-$, $AlCl_4^-$, $SbF_6^-$, $CF_3SO_3^-$, $(CF_3SO_2)_2N^-$, and $-B(A)_x(A')_y$ where A is alkyl, A' is aryl, and $x+y=4$. These materials suffer from one or more of the disadvantages of thermal instability ($BF_4^-$, $PF_6^-$, and $AsF_6^-$), potentially explosive character ($ClO_4^-$), being electrochemically non-passivating upon reduction ($AlCl_4^-$, $SbF_6^-$), affording electrolytes having marginally adequate conductivities for many applications ($CF_3SO_3^-$), and difficulty in preparation and purification ($B(A)_x(A')_y^-$). These deficiencies of available electrolyte salts have retarded the development of light metal anode batteries having optimized capacities and reduced weights. Use of presently-available electrolyte salts has resulted in batteries having sub-optimal performance characteristics such as limited operating temperature ranges and limited discharge/charge rate performance.

U.S. Pat. No. 4,505,997 of Armand discloses bis(perhalogenoacyl or perhalogenosulfonyl) imides of certain metals, for use in battery electrolytes. Armand's compounds have the general formula $(C_nX_{2n+1}Y)_2N^-M^+$ in which X is a halogen, n is an integer from 1–4, Y is a CO or $SO_2$ group, and M is an alkali metal, preferably lithium or sodium, and possibly potassium. These materials appear to offer good thermal stability, but their conductivities in nonaqueous matrices are lower than desirable.

In a paper by Turowsky and Seppelt published in Inorg. Chem., 27, 2135–2137 (1988), the trisubstituted methane compound $(CF_3SO_2)_3CH$ and four of its salts were disclosed in the context of an attempt to form a stable xenon-carbon bond. In the course of the investigation the K, Rb, Cs, and Ag salts of the tris(trifluoromethylsulfonyl) methane were prepared. Although the related anion $(CF_3SO_2)_2N^-$ had been reported to form a chemical bond to xenon, Turowsky and Seppelt were unsuccessful in achieving a carbon-xenon bond with their compound. The ability of $(CF_3SO_2)N^-$ to form Xe—N bonds indicates the nitrogen is quite electrophilic, even though it is the formal site of negative charge, and that the electron density is actually quite delocalized through the anion. Negative charge delocalization is a property shared by the anions of highly conductive Li salts of organic anions. The failure of $(CF_3SO_2)_3C^-$ to bond to xenon suggests the central carbon retains greater negative charge density and would suggest that $Li(CF_3SO_2)_3$ would exhibit low conductivities.

U.S. Pat. No. 4,049,861 of Nozari generically discloses highly fluorinated aliphatic sulfonic and sulfonylic compounds as catalysts useful in the preparation of abrasion resistant coatings. The compound $(CF_3SO_2)_3CH$ was exemplified in a table, and metal salts of this and related compounds containing highly fluorinated alkyl groups are mentioned. This reference does not teach how to make any of the compounds within its generic disclosure, and does not suggest that such compounds have any other uses besides the catalytic utility disclosed.

A need exists for improved electrolyte salts for use in electrochemical cells which employ light metal anodes, for electrolytes containing such salts, and for improved batteries containing such electrolytes. Such improved electrolyte salts, electrolytes, and batteries are the subject of the present invention.

SUMMARY OF THE INVENTION

According to the present invention electrochemical cells and batteries are provided having electrolytes formed from conductive salts of improved properties for such applications. The electrochemical cells or batteries have anodes which are made of or include metals of typically light atomic weight.

The salts of the invention, in addition to having surprisingly high conductivities, offer the advantages of improved thermal stability, and nonaqueous electrolytes which include these salts possess generally improved conductivities. The relatively high electrolyte conductivities presumably result from low ion pairing tendencies of the anions, as a result of reduced negative charge density in the central carbon atom by the three strongly electron withdrawing substituent groups attached thereto. Steric hindrance probably also leads to reduced ion pairing which avoids the resulting degradation in electrolyte performance. A related advantage is that the conductive salts of the invention are generally quite soluble in the nonaqueous matrices employed in the electrolytes. For example, $LiC(CF_3SO_2)_3$ is soluble in $CH_3CN$ to at least 5M. The high concentrations of salt which are therefore obtainable in the electrolyte result in low concentration polarization effects during the operation of electrochemical cells containing such electrolytes.

An exemplary compound of the invention useful as electrolytes in nonaqueous matrices have the formula shown as I below.

In formula I, the symbol $M^{n+}$ indicates an ion of a metal of typically light atomic weight. The groups Y, Y', and Y" each may be an $>SO_2$ or $>CO$ moiety. The groups R and R' are separate halogenated alkyl groups of 1-4 carbon atoms, respectively, or are joined together to constitute a halogenated alkylene radical of from 2-4 carbon atoms linking the groups Y and Y' and forming a ring structure which includes R, R', Y, Y' and the carbon atom to which Y and Y' are attached. The group R" is an alkyl radical of 1-4 carbon atoms, a haloalkyl radical of 1-4 carbon atoms, or a halogenated phenyl group. In another exemplary compound, the —Y"—R" group is replaced by Z, which is an electron-withdrawing substituent selected from the group consisting of —C(O)H, —NO₂, —CN, —F, and perfluorinated alkyls and aryls containing no more than 8 carbons. Z may also be substituent having an assigned Hammet sigma(-meta) value greater than +0.4. The subscript n is an integer of 1-3 which depends on the identify of metal ion $M^{n+}$.

An electrochemical cell or battery of the invention comprises an anode, a cathode, and a nonaqueous electrolyte which includes an ionizable compound as described above, in contact with the anode and cathode.

BRIEF DESCRIPTION OF THE DRAWING

The invention will be more completely understood from a consideration of the following detailed description taken in conjunction with the drawing, in which.

DETAILED DESCRIPTION

Figure 1:
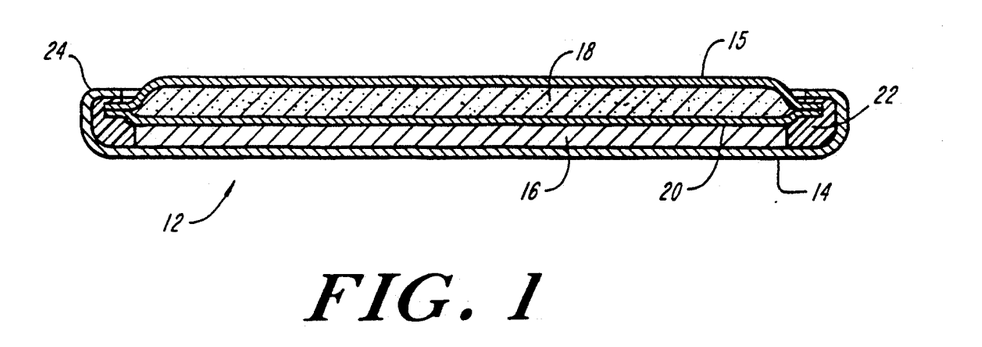
FIG. 1 shows an arrangement of components of a cell utilizing the present invention.

The present invention contemplates a cell, such as cell 12 of FIG. 1, having within a conductive container 14 and cover 15, an anode 16 and a cathode particle mix 18. A separator 20 which includes an electrolyte is placed between the anode and the mix. Container 14 is crimped at the edges 24 capturing cover 15 under an insulating gasket 22. The cells so formed may be configured for either parallel or series operation.

The salt bearing electrolytes in one exemplary embodiment having the formula:

The compounds of structural formula I which are useful as the charge carrying material in nonaqueous electrolytes are those in which $M^{n+}$ is an ion of Li, Na, K, Ca, Mg, Zn or Al. Of these, Na, Ca, Mg are preferred, and Li is most preferred.

The groups Y, Y', and Y" are preferably $SO_2$ moieties.

The groups R, R', and R" each preferably contains one or two carbon atoms, with one carbon atom being most preferred. These groups are preferably halogenated with fluorine and chlorine, the most preferred halogen being fluorine, and are preferably perhalogenated.

In another exemplary compound of the invention useful as a salt-bearing electrolyte, the —Y"—R" group is replaced with Z, which is a strongly electron-withdrawing substituent selected from the group consisting of —C(O)H, —NO₂, —CN, —F, and perfluorinated alkyls and aryls containing no more than 8 carbons. In a further exemplary compound, the strongly electron-withdrawing substituent has an assigned Hammett sigma(meta) value greater than +0.4. Reference is made to C. D. Ritchie and W. F. Sager in Prog. Phys. Org. Chem., Vol. 2, p. 323 (1964), for definitions and a partial list of substituents.

The anode 16 of the electrochemical cell is preferably lithium metal. It may be used as a pure foil, carried on aluminum foil backing or pressed into axpanded metal screen and alloyed with various other metals. The lithium may also be intercalated into a host material such as carbon or inorganic and/or organic low potential host materials that are intercalatable.

The cathodes 18 of the electrochemical cell of the invention are generally particles of an active material bound into a plastic material such as ethylene/propylene/diene monomer (EPDM) terpolymer, or particles of an active material mixed in a binder of carbon, emulsified Teflon, or both, which is in turn pressed into an expanded metal screen. In polymer electrolyte batteries the polymer electrolyte can act as the active material binder.

The active material of the cathode of a primary battery may be any of the commonly employed reducible materials such as $MnO_2$, $CuCl_2$, $CoO_2$, $CF_x$, etc. The active material of the cathode of a rechargeable electrochemical cell or battery is generally either a cathodic host material such as $TiS_2$, $NbSe_3$, $MnO_2$, $TaS_2$, $MoS_3$, $MoS_2$, $V_6O_{13}$, $V_2O_5$, $FeS_2$, $CoO_2$, $Cr_3O_8$ etc. or an organic polymer such as polyaniline or polythiophene.

In such a rechargeable electrochemical cell or battery, discharge involves oxidation of the active metal of the anode, corresponding reduction of the cathodic host material, and neutralization of the charge on the cathode by migration of the ions of anodic material into host planes or channels of the cathodic host material, where they take up residence. On recharging, the metallic ions of the anodic material leave the cathodic host material and return to the anode where they are reduced, and the cathodic host material is reoxidized.

The preferred cathodic materials of this invention are $TiS_2$ which is a layered (lamellar or planar) compound and various phases, mixed phases and stoichiometries of the oxides of manganese, vanadium, cobalt and nickel.

The cathode of the electrochemical cell or battery of the invention may include polymeric material and an ionizable compound of the invention to provide the requisite ionic conductivity. Alternatively polymeric active cathode material may contain functionalities which are able to be oxidized and reduced.

A variety of fluorinated sulfonylfluoride materials useful for the synthesis of the compounds of this invention are available from 3M Industrial Chemical Products Division Laboratory, St. Paul, Minn. Methylheptafluoropropyl ketone is commercially available from PCR, Inc., Gainesville, Fla. Bis(trifluoromethylsulfonyl)methane employed in the synthesis below is available from 3M.

Synthesis of Lithium Perfluoromethylsulfonyl Methide

This material was prepared substantially according to the method of Turowsky and Seppelt to yield the acidic trisubstituted methane, which was in turn converted to the lithium salt. 48 ml (0.144 moles) of 3M methylmagnesium chloride Grignard reagent in THF was added slowly with cooling to 20 g (0.072 moles) of bis(trifluoromethylsulfonyl)methane in 150 ml of THF, under an argon atmosphere in a glove box. Near the end of the Grignard reagent addition step a fine white precipitate of $(CF_3SO_2)_2C^{2-}(MgCl^+)_2$ began to form. This slurry was transferred to a Parr bomb, which was sealed and chilled to about $-40°$ C. To this was added 16.4 g (0.108 moles) of $CF_3SO_2F$ through a valve, and the apparatus was then hermetically sealed. The bomb was warmed to 70° C., held at this temperature and 120-140 psi for 48 hours, cooled to room temperature, and opened. The solvent and volatiles were removed under vacuum, and the remaining solids were dissolved in water and acidified to a pH of less than 1. The resulting two-phase system was extracted three times with ether, the solvent was removed, and the crude tris(trifluoromethylsulfonyl)methane product was stored in a freezer and subsequently distilled under vacuum at about 70° C. and condensed on a cold finger cooled by acetone/dry ice. The resulting purified product was titrated with lithium methoxide in methanol to yield the corresponding lithium salt in 50% yield. Characterization: The melting point=268° C.; $^{13}C$ NMR evaluation in acetone $d_6$ shows resonances at +123.27 PPM and at +119.08 PPM relative to TMS. The FTIR spectrum is essentially identical to that of the Cs salt.

Preparation of Li methides where Z is selected from —C(O)H, —NO₂, —CN, —F, and perfluorinated alkyls and aryls The difluoromethylsulfonyl carbanion is prepared by double deprotonation with a Grignard reagent, as described above. The resultant activated methylene carbanion is reacted, in an $SN_2$ displacement reaction, with an electrophilic reagent which contains the desired Z group bonded to a good leaving group. Exemplary reagents for specific Z groups, which are commercially available, are given below.

| ELECTROPHILIC REAGENTS FOR $SN_2$ ADDITION TO ACTIVATED METHYLENE CARBANION[1] | | |
|---|---|---|
| R group | Reagent | Leaving group |
| Z = F | CH₃—⟨◯⟩—SO₂—N(F)—CH₃<br>(N-fluoro-N-methyl-p-toluenesulfonamide)<br>(Aldrich Chemical Co., Milwaukee, WI) | CH₃—⟨◯⟩—SO₂N⁻—CH₃ |
| Z = CN | N≡C—Br<br>(cyanogen bromide)<br>(Aldrich Chemical Co., Milwaukee, WI) | Br⁻ |
| Z = NO₂ | O₂NO—C(CH₃)(CH₃)—C≡N<br>(acetone cyanohydrin nitrate)<br>(Columbia Organics, Camden, SC) | N≡C⁻ and CH₃COCH₃ (acetone) |

-continued
ELECTROPHILIC REAGENTS FOR SN2 ADDITION TO ACTIVATED METHYLENE CARBANION[1]

| R group | Reagent | Leaving group |
|---|---|---|
| Z = CF₃ |  (trifluoromethyldibenzothiophenium triflate) (Daiken Industries, Osaka, JAPAN) |  and $^-O_3SCF_3$ (triflate) |

[1]The dianion starting material is the same in every synthesis, $(CF_3SO_2)_3C^{-2}$. Each reagent is just an available electrophilic source of the desired Z group.

Preparation of a mixed alkyl/perfluoroalkylsulfonyl methide salt $$CH_3SO_2CH_3 \xrightarrow[THF]{CH_3MgCl} \xrightarrow{CF_3SO_2F}$$
$$CH_3SO_2-CH_2-SO_2CF_3$$

| 1) K⁺ t-butoxide
| 2) CF₃SO₂F
| 3) H⁺/ether extraction
↓

$$\underset{CH_3SO_2C(SO_2CF_3)_2}{\overset{Li^\oplus\,\ominus}{}} \xleftarrow[MeOH]{CH_3OLi} CH_3SO_2CH(SO_2CF_3)_2$$

One equivalent of methylmagnesium chloride Grignard reagent is added slowly at room temperature to dimethyl sulfone in THF under an inert atmosphere. The mixture is transferred to a Parr bomb and chilled to about −50° C. One equivalent of perfluoromethylsulfonyl fluoride is added. The bomb is sealed, warmed to about 70° C., held at that temperature for about 48 hours, and occasionally stirred. It is then cooled to room temperature, and the pressure is released. Two equivalents of a weak hindered base are added to remove the more acidic protons of the central carbon. One equivalent of perfluoromethylsulfonyl fluoride is condensed in. The bomb is resealed, warmed to 70° C., and held at that temperature for about 48 hours. After the bomb is cooled to room temperature and the pressure released, the resulting solution is acidified to a pH of about 1 with aqueous HCl and extracted three times into ether. The ether is removed under vacuum and the residue is distilled under vacuum and condensed onto a cool surface to obtain the parent acid. Titration with lithium methoxide in anhydrous methanol and removal of solvent yields the desired new lithium salt.

Preparation of a Mixed Cyclic/Acyclic Perfluoroalkylsulfonyl Methide Salt $$CF_3SO_2F + CH_3MgCl \longrightarrow CF_3SO_2CH_3$$

| 1) LDA
| 2) FSO₂(CF₂)₃SO₂F
↓

Trifluoromethylsulfonyl fluoride is reacted with one equivalent of methylmagnesiumbromide Grignard reagent to yield methyl trifluoromethylsulfone, which is in turn treated with one equivalent of a sterically hindered base such as LDA to remove a proton and form the anion of the sulfone. A halogenated or fluorinated material containing two terminal sulfonyl fluoride moieties is added to form a disulfone having a terminal sulfonyl fluoride group. Upon addition of a further equivalent of hindered base to remove one of the protons between the two sulfone moieties, the resulting anion undergoes ring closure, forming the desired trisubstituted methane. The reaction mixture is acidified, the product is extracted into ether, and finally titrated with lithium methoxide in methanol to yield the desired methide salt.

Preparation of an Aryl Substituted Perfluoroalkylsulfonyl Methide Salt $$C_6F_5SO_2F + CH_3MgBr \longrightarrow C_6F_5SO_2CH_3$$

| 1) CH₃MgBr
| 3) CF₃SO₂F
↓

Pentafluorophenylsulfonyl fluoride is treated with one equivalent of methylmagnesium bromide to yield the expected pentafluorophenylmethyl sulfone. This is then treated with a second equivalent of Grignard reagent and the intermediate which forms is allowed to react with a halogenated or fluorinated alkylsulfonylfluoride to form a disulfone. Treating this further with Grignard reagent and halogenated alkylsulfonyl fluoride produces the desired trisubstituted methane. This is acidified, extracted into ether, and converted to the corresponding lithium salt as before.

Preparation of a Symmetric Perfluoroalkylcarbonyl Methide Salt $CF_3CCH_2CCF_3$ and $CF_3CF$ commercially available from PCR Chemicals, Gainesville, FL 1,1,1,5,5,5-hexafluoro-2,4-pentanedione is treated with two equivalents of LDA to produce the expected dianion. This is in turn treated with one equivalent of perfluoroacetylfluoride to produce the desired product in crude form. The reaction mixture is acidified and the trisubstituted methane product is extracted into ether, sublimed, and subsequently titrated with lithium methoxide in methanol to yield the desired methide salt.

Preparation of an Asymmetric Perfluoroalkylcarbonyl Methide Salt

An unsymmetrical methyl ketone such as methylheptafluoropropyl ketone is treated successively with an equivalent of a hindered base such as LDA, then with a halogenated or fluorinated acid halide or fluoride to produce an intermediate β-diketone. This is again treated with an equivalent of hindered base and a halogenated acid halide to form the desired trisubstituted methane. The reaction mixture is subsequently acidified, the product is extracted into ether, and then treated with lithium methoxide in methanol to form the desired lithium methide salt.

Although the above examples illustrate the preparation of a variety of lithium methide salts, salts of other metals such as Na, Mg, Ca, Al, and Zn are prepared similarly, by titrating the acidic trisubstituted methane with a solution of a basic salt of the metal of interest. Nonaqueous titrations in solvents such as methanol are preferred because of the relative ease of solvent removal. However, the reactions can also be carried out in aqueous solution and the desired salts recovered by removal of the water under vacuum and gentle heating.

A compound of the invention is employed in a battery electrolyte by dissolving it in an appropriate anhydrous solvent to give a conductive solution, and employing this solution as the electrolyte in an electrochemical cell or battery constructed as known to the art. The salt is preferably employed at a concentration such that the conductivity of the electrolyte solution is at or near its maximum value, although a wide range of other concentrations will also serve.

Electrolytes for use in rechargeable or secondary batteries must contain a metal ion of the anode active material. In the case of primary batteries, the electrolyte will contain anions of the invention, but the cations of the electrolyte salt or salts may under certain circumstances be materials other than the metal ion of the anode active material, provided that the salt or salts employed meet the commonly accepted requirements of primary nonaqueous battery electrolytes. These requirements include, but are not restricted to, providing sufficiently highly conducting electrolyte solutions, having electrolyte solutions which are stable in contact with the anode, and having electrolyte solutions which provide acceptable kinetics of reaction with the cathode during cell discharge.

Conductivities were measured for three 1.0M lithium salts in tetrahydrofuran at 25° C. The results are presented in the Table below.

| Salt | Conductivity (Scm$^{-1}$) |
| --- | --- |
| LiCF$_3$SO$_3$ (Triflate) | 6.0 × 10$^{-4}$ |
| LiN(CF$_3$SO$_2$)$_2$ (Imide) | 1.0 × 10$^{-2}$ |
| LiC(CF$_3$SO$_2$)$_3$ (Methide) | 1.2 × 10$^{-2}$ |

Experimental lithium cells were fabricated according to the invention. The cells were cathode limited with a cathode capacity of 4.5 mAh/cm$^2$. The active material in the cathode was TiS$_2$ and the electrolyte was 1.5 molar LiC(CF$_3$SO$_2$)$_3$ in base-treated tetrahydrofuran. A Celgard 2400 separator was used. The open circuit voltages of the filled cells were 3.0 volts. The experimental cells yielded over twenty discharge-charge cycles with unpurified LiC(CF$_3$SO$_2$)$_3$ indicating viability of the new salt for both primary and secondary applications.

Polymer electrolyte cells were also prepared and tested. A cell comprising a Li anode, TiS$_2$ cathode and LiC(CF$_3$SO$_2$)$_3$ in a polymer matrix of poly(bis-(methoxyethoxyethoxide)phosphazene), i.e. MEEP which had a ratio of MEEP monomer to salt of 5-to-1 achieved over thirty-six discharge-charge cycles.

Other embodiments of the invention will be apparent to those skilled in the art from a consideration of this specification or practice of the invention disclosed herein. It is intended that the specification and examples be considered as exemplary only, with the true spirit and scope of the invention being indicated by the following claims.

I claim:

1. An electrochemical cell, comprising
   an anode;
   a cathode; and
   an electrolyte which comprises a nonaqueous matrix and an ionizable compound, said ionizable compound being in said nonaqueous matrix and having the formula wherein
   Y, Y', and Y" are each selected from the group consisting of $>SO_2$ and $>CO_2$;
   R and R' are separate halogenated alkyl groups of 1–4 carbon atoms, respectively, or are joined together to constitute a unitary halogenated alkylene radical of from 2–4 carbon atoms linking Y and Y' and forming a ring structure which includes R, R', Y, Y', and the carbon atom to which Y and Y' are attached; and
   R" is selected from the group consisting of alkyl radicals of 1–4 carbon atoms, haloalkyl radicals of 1–4 carbon atoms, and halogenated phenyl groups;
   said electrolyte contacting both said anode and said cathode.

2. The electrochemical cell of claim 1 wherein said anode comprises $Li^+$.

3. The electrochemical cell of claim 1 wherein said cathode comprises polymeric material and said ionizable compound.

4. The electrochemical cell of claim 3 wherein said polymeric material includes functionalities which may be oxidized and reduced.

5. The electrochemical cell of claim 1 wherein in said ionizable compound at least two of Y, Y', and Y" are $>SO_2$ groups.

6. The electrochemical cell of claim 1 wherein in said ionizable compound, Y, Y', and Y" are $>SO_2$ groups.

7. The electrochemical cell of claim 1 wherein in said ionizable compound, R and R' contain halogen atoms selected from the group consisting of fluorine and chlorine, and are perhalogenated.

8. The electrochemical cell of claim 1 wherein in said ionizable compound, R, R', and R" contain halogen atoms selected from the group consisting of fluorine and chlorine.

9. The electrochemical cell of claim 1 wherein in said ionizable compound, R, R', and R" are perfluorinated.

10. The electrochemical cell of claim 1 wherein in said ionizable compound, R, R', and R" each contains 1–2 carbon atoms.

11. The electrochemical cell of claim 1 wherein the nonaqueous matrix of said electrolyte is a nonaqueous liquid.

12. The electrochemical cell of claim 1 wherein the nonaqueous matrix of said electrolyte comprises a polymer.

13. The electrochemical cell of claim 1 wherein said electrolyte comprises lithium tris(trifluoromethylsulfonyl)methide.

14. A composition for use as an electrolyte, comprising:
    a nonaqueous matrix; and
    an ionizable compound, said ionizable compound being in said nonaqueous matrix and having the formula wherein
   Y, Y', and Y" are each selected from the group consisting of $>SO_2$ and $>CO_2$;
   R and R' are separate halogenated alkyl groups of 1–4 carbon atoms, respectively, or are joined together to constitute a unitary halogenated alkylene radical of from 2–4 carbon atoms linking Y and Y' and forming a ring structure which includes R, R', Y, Y', and the carbon atom to which Y and Y' are attached; and
   R" is selected from the group consisting of alkyl radicals of 1–4 carbon atoms, haloalkyl radicals of 1–4 carbon atoms, and halogenated phenyl groups.

15. The composition of claim 14 further comprising polymeric material and said ionizable compound.

16. The composition of claim 15 wherein said polymeric material includes functionalities which may be oxidized and reduced.

17. The composition of claim 14 wherein in said ionizable compound at least two of Y, Y', and Y" are $>SO_2$ groups.

18. The composition of claim 14 wherein in said ionizable compound, Y, Y', and Y" are $>SO_2$ groups.

19. The composition of claim 14 wherein in said ionizable compound, R and R' contain halogen atoms selected from the group consisting of fluorine and chlorine, and are perhalogenated.

20. The composition of claim 14 wherein in said ionizable compound, R, R', and R" contain halogen atoms selected from the group consisting of fluorine and chlorine.

21. The composition of claim 14 wherein in said ionizable compound, R, R', and R" are perfluorinated.

22. The composition of claim 14 wherein in said ionizable compound, R, R', and R" each contains 1–2 carbon atoms.

23. The composition of claim 14 wherein the nonaqueous matrix of said electrolyte is a nonaqueous liquid.

24. The composition of claim 14 wherein the nonaqueous matrix of said electrolyte comprises a polymer.

25. The composition according to claim 14 wherein said ionizable compound is lithium tris(trifluoromethylsulfonyl)methide.

26. A compound having the formula:

wherein
- Y and Y' are each selected from the group consisting of $>SO_2$ and $>CO_2$;
- R and R' are separate halogenated alkyl groups of 1-4 carbon atoms, respectively, or are joined together to constitute a unitary halogenated alkylene radical of from 2-4 carbon atoms linking Y and Y' and forming a ring structure which includes R, R', Y, Y', and the carbon atom to which Y and Y' are attached; and
- Z is a strongly electron withdrawing substituent selected from the group consisting of $-NO_2$, $-CN$, $-F$, and perfluorinated alkyls and aryls containing no more than 8 carbons.

27. An electrochemical cell, comprising
an anode;
a cathode; and
an electrolyte which comprises a nonaqueous matrix and an ionizable compound, said ionizable compound being in said nonaqueous matrix and having the formula wherein
- Y and Y' are each selected from the group consisting of $>SO_2$ and $>CO_2$;
- R and R' are separate halogenated alkyl groups of 1-4 carbon atoms, respectively, or are joined together to constitute a unitary halogenated alkylene radical of from 2-4 carbon atoms linking Y and Y' and forming a ring structure which includes R, R', Y, Y', and the carbon atom to which Y and Y' are attached; and
- Z is a strongly electron withdrawing substituent selected from the group consisting of $-NO_2$, $-CN$, $-F$, and perfluorinated alkyls and aryls containing no more than 8 carbons.

28. A composition for use as an electrolyte, comprising:
a nonaqueous matrix; and
an ionizable compound, said ionizable compound being in said nonaqueous matrix and having the formula wherein
- Y and Y' are each selected from the group consisting of $>SO_2$ and $>CO_2$;
- R and R' are separate halogenated alkyl groups of 1-4 carbon atoms, respectively, or are joined together to constitute a unitary halogenated alkylene radical of from 2-4 carbon atoms linking Y and Y' and forming a ring structure which includes R, R', Y, Y', and the carbon atom to which Y and Y' are attached; and
- Z is a strongly electron withdrawing substituent selected from the group consisting of $-NO_2$, $-CN$, $-F$, and perfluorinated alkyls and aryls containing no more than 8 carbons.

* * * * *

UNITED STATES PATENT AND TRADEMARK OFFICE
CERTIFICATE OF CORRECTION

PATENT NO. : 5,273,840
DATED : December 28, 1993
INVENTOR(S) : Lawrence A. Dominey

Page 1 of 2

It is certified that error appears in the above-indentified patent and that said Letters Patent is hereby corrected as shown below:

In the Abstract, 5th and 6th line from the bottom, " -Y-"R" " should read -- -Y"-R" --.

Column 4, line 43, "axpanded" should read --an expanded--.

Column 6, in the Table entitled "ELECTROPHILIC REAGENTS FOR $SN_2$ ADDITION TO ACTIVATED METHYLENE CARBANION[1]", the formula for cyanogen bromide which presently reads "N=C-Br" should read --N≡C-Br--; the formula for acetone cyanohydrin nitrate which presently reads:

should read:

and the cyanate leaving group which presently reads "N=C-" should read -- N≡C⁻ --.

UNITED STATES PATENT AND TRADEMARK OFFICE
CERTIFICATE OF CORRECTION

PATENT NO. : 5,273,840
DATED : December 28, 1993
INVENTOR(S) : Lawrence A. Dominey It is certified that error appears in the above-indentified patent and that said Letters Patent is hereby corrected as shown below:

Column 9, at the top of the column, the reaction which reads:

$$C_6F_5SO_2CH(SO_2CF_3)_2 \xrightarrow{CH_3OLi} C_6F_5SO_2\overset{Li^+}{\underset{\ominus}{C}}(SO_2CF_3)$$

should read:

$$C_6F_5SO_2CH(SO_2CF_3)_2 \xrightarrow{CH_3OLi} C_6F_5SO_2\overset{Li^+}{\underset{\ominus}{C}}(SO_2CF_3)_2$$

Signed and Sealed this

Eighteenth Day of October, 1994

Attest:

Bruce Lehman

BRUCE LEHMAN

*Attesting Officer*        *Commissioner of Patents and Trademarks*